United States Patent [19]

Nagatsu et al.

[11] Patent Number: 4,891,440

[45] Date of Patent: Jan. 2, 1990

[54] PROCESS FOR PRODUCING UNSATURATED QUATERNARY AMMONIUM SALTS

[75] Inventors: Yoshirou Nagatsu; Akiyoshi Nagamoto; Kazuya Harada; Hideaki Mukouyama, all of Yatsushiro-city, Japan

[73] Assignee: Kohjin Co., Ltd., Tokyo, Japan

[21] Appl. No.: 290,045

[22] PCT Filed: Feb. 18, 1988

[86] PCT No.: PCT/JP88/00165

§ 371 Date: Oct. 13, 1988

§ 102(e) Date: Oct. 13, 1988

[87] PCT Pub. No.: WO88/06152

PCT Pub. Date: Aug. 25, 1988

[30] Foreign Application Priority Data

Feb. 18, 1987 [JP] Japan .................................. 62-33192

[51] Int. Cl.$^4$ .............................................. C07L 69/52
[52] U.S. Cl. .................................................. 560/222
[58] Field of Search ........................................ 560/222

[56] References Cited

PUBLICATIONS

CA 82(16): 99986d.
CA 87(16):120502h.
CA 93(10): 984802.
CA 106(14):102702e.

*Primary Examiner*—Paul J. Killos
*Attorney, Agent, or Firm*—Oliff & Berridge

[57] ABSTRACT

High grade quaternary ammonium salts represented by the following General Formula II:

$$\begin{array}{c} R_1 \\ | \\ CH_2=C \quad\quad R_2 \\ | \quad\quad\quad | \\ O=C-A-B\overset{+}{-}N-R_3.X^- \\ | \\ R_4 \end{array} \quad \text{II}$$

(in which $R_1$ represents a hydrogen atom or a methyl group; $R_2$ and $R_3$ independently represents an alkyl group containing 1 to 4 carbon atoms; A represents an oxygen atom or an —NH— group; B represents an alkylene group containing 1 to 4 carbon atoms; $R_4$ represents an alkyl group or a benzyl group; and $X^-$ represents a halogen anion) can be produced by reacting a cationic vinyl monomer represented by the following General Formula I:

$$\begin{array}{c} R_1 \\ | \\ CH_2=C \quad\quad\quad R_2 \\ | \quad\quad\quad\quad / \\ O-C-A-B-N \\ \quad\quad\quad\quad \backslash \\ \quad\quad\quad\quad R_3 \end{array} \quad \text{I}$$

(in which $R_1$, $R_2$, $R_3$, A and B have the same meanings as defined above) with an alkyl halide or an aralkyl halide in a medium consisting of a particular mixture of water and an aprotic organic solvent under a condition where the concentration of oxygen dissolved in the reaction system is lower than 1.8 ppm but not less than 0.3 ppm. The reaction proceeds quite smoothly, without forming deposition of quaternary ammonium salts produced by the reaction. The overheating of the reaction system, which is a cause for the generation of gelation-causing substances and polymerization inhibitors, can be prevented effectively since the reaction mixture can be smoothly stirred and hence the generated heat can be efficiently removed therefrom. The process therefore enables to produce on a commercial scale aqueous solutions of unsaturated quaternary ammonium salts of very high quality which can be used as a raw material for producing cationic polymers of high molecular weight.

3 Claims, No Drawings

PROCESS FOR PRODUCING UNSATURATED QUATERNARY AMMONIUM SLATS

FIELD OF THE INVENTION

The present invention relates to a process for producing unsaturated quaternary ammonium salts represented by General Formula II:

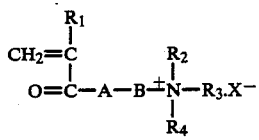

(in which $R_1$ represents a hydrogen atom or a methyl group; $R_2$ and $R_3$ each represents an alkyl group containing 1 to 4 carbon atoms; A represents an oxygen atom or an —NH— group; B represents an alkylene group containing 1 to 4 carbon atoms; $R_4$ represents an alkyl group containing 1 to 4 carbon atoms or a benzyl group; and $X^-$ represents a halogen anion) which comprises treating cationic vinyl monomers represented by General Formula I:

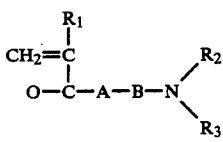

(in which $R_1$, $R_2$, $R_3$, A and B have the same me as defined above) with an alkyl halide or an aralkyl halide. More particularly, it relates to a process for producing unsaturated quaternary ammonium salts of very high quality which contain impurities in only small quantities.

Homopolymers or water-soluble copolymers of the unsaturated quaternary ammonium salts represented by general formula II are highly useful water soluble cationic polymers utilizable as an agent for improving the yield of various additives upon paper making; as an agent for improving filtration of water upon paper making; as an agent for recovering white water; as an agent for processing fibrous pulp; as an filtration aid for sludge; or as a polymeric flocculant.

PRIOR ART

In one known process for producing such unsaturated quaternary ammonium salts, unsaturated tertiary amines are converted into corresponding quaternary salts by being allowed to react with an alkyl halide or an aralkyl halide in an organic medium. It is however not preferable to produce the quaternary ammonium salts of General Formula II in an organic solvent system which exhibits a chain transfer effect. This is because polymerization of the quaternary ammonium salts or copolymerization thereof with other monomers is generally carried out in an aqueous medium since polymers of the salts are employed in an aqueous solution. In view of the above, there have been proposed in recent years various processes for producing the unsaturated quaternary salts in an aqueous medium.

In connection with this, there have been presented two problems to be taken into consideration upon production of the quaternary salts from the unsaturated tertiary amines.

Firstly, the cationic monomers represented by General Formula I or II are monomers having an extremely high polymerizability. As is well known, various proposals have been made for the prevention of their polymerization during production or storage. For example, Japanese Patent Publication No. 10,340/84 discloses that the polymerization of the quaternary ammonium salts of dialkylaminoalkyl (meth)acrylates occurs when the amount of oxygen dissolved in the aqueous solution thereof is small and that the polymerization of the salts dissolved in an aqueous solvent can be prevented by incorporating 50 to 1,000 ppm (based on the quaternary salts) of polymerization inhibitors and 1.8 ppm or more (based on the aqueous solution) of oxygen into the aqueous solution.

Secondly, there is a serious disadvantage that, in cases where the unsaturated quaternary ammonium salts are produced in water, the corresponding tertiary amines are susceptible to hydrolysis (in particular, in the cases where the tertiary amines are aminoesters represented by General Formula I in which A is an oxygen atom), and hence (meth)acrylic acid tends to be formed as a by-product. The desired unsaturated quaternary ammonium salts are cationic monomers based on their structure, whereas (meth)acrylic acid formed by the hydrolysis is an anionic monomer. Accordingly, if the polymerization is carried out in the presence of both of the monomers, there is formed a water-soluble substance, i.e., so-called ion complex. Consequently, the resulting polymer could not fully exhibit its effect as a polymeric electrolyte. It is therefore necessary that the desired unsaturated quaternary ammonium salts do not contain such a hydrolyzed product. Because of this, it has been attempted, for example, to remove hydrolyzed products from crude unsaturated quaternary ammonium salts or to prevent the undesired hydrolysis of tertiary amines to take place. In the former, unsaturated quaternary ammonium salts are extracted from a crude reaction product, in order to remove the hydrolyzed products. However, this method is unpractical since the efficiency of the extraction is poor, a large quantity of solvents must be used, and the extraction step must be carried out repeatedly. As basic measures for preventing the hydrolysis, there have been attempted to enhance the concentration of the unsaturated tertiary amines as high as possible, to carry out the reaction at a low temperature, and to add water by portions so as to make the contact time with water as short as possible. However, these measures proved to be only unsatisfactory The inventors have previously proposed to convert the unsaturated tertiary amines into quaternary salts in a medium consisting of a mixture of water and an aprotic organic solvent (Japanese Patent Publication No. 46,467/76).

This method gives satisfactory results with regard to the prevention of the formation of (meth)acrylic acid due to the hydrolysis of the amines represented by General Formula I.

However, with regard to the production of cationic polymers from cationic monomers, such as those shown by General Formula II, it has been more strongly desired in recent years to obtain cationic polymers having further improved properties (for example, highly cationic copolymers containing more than 30% by weight of the cationic monomers, or high molecular weight cationic copolymers having an average molecular weight of $10^7$ or more) which are suited for such uses as those described hereinabove. In order to produce such (co)polymers, it has been desired to prepare unsaturated quaternary ammonium salts having a further improved quality. It has been pointed out that important requirements for such high quality unsaturated quaternary ammonium salts are (1) the amount of (meth)acrylic acid (or by-product formed by hydrolysis) should be as small as possible and (2) the salts should not contain polymerization inhibitors, such as divinyl compounds, even in a trace amount.

However, in the prior art, the concentration of oxygen dissolved in the reaction system must be increased in order to inhibit the polymerization of the reaction products. This causes the problem that the generation of substances that causes gelation (e.g., divinyl compounds), as well as the generation of polymerization inhibitors, could not be suppressed to a sufficient degree.

DETAILED DESCRIPTION OF THE INVENTION

The inventors have conducted intensive investigations on a process for producing unsaturated quaternary ammonium salts where hydrolyzed products are produced in only small quantities and the generation of gelation-causing substance and the polymerization inhibitors can be suppressed. As a result, it has now been found that, when a medium consisting of a particular mixture of water and an aprotic organic solvent is used, although the concentration of oxygen dissolved in the reaction system is lower than 1.8 ppm, the polymerization of the reaction products does not proceed and the by-products are generated in only very limited amounts.

Accordingly, there is provided by the present invention a process for producing unsaturated quaternary ammonium salts of very high quality represented by the following General Formula II:

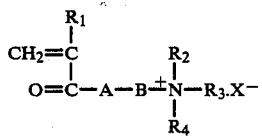

II (in which $R_1$ represents a hydrogen atom or a methyl group; $R_2$ and $R_3$ each represents an alkyl group containing 1 to 4 carbon atoms; A represents an oxygen atom or an —NH— group; B represents an alkylene group containing 1 to 4 carbon atoms; $R_4$ represents an alkyl group containing 1 to 4 carbon atoms or a benzyl group; and $X^-$ represents a halogen atom) which process comprises reacting a cationic vinyl monomer represented by the following General Formula I:

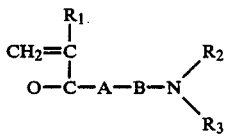

I (in which $R_1$, $R_2$, $R_3$, A and B have the same meanings as defined above) with an alkyl halide or an aralkyl halide in a medium consisting of a particular mixture of water and an aprotic organic solvent under a condition that the concentration of oxygen dissolved in the reaction system is lower than 1.8 ppm but not less than 0.3 ppm.

As examples of unsaturated tertiary amines of General Formula I to be used in the invention, mention may be made of N,N-dimethylaminoethyl acrylate, N,N-diethylaminoethyl acrylate, N,N-dimethylaminopropyl acrylate, N,N-diethylaminopropyl acrylate and corresponding methacrylates, N,N-dimethylaminoethylacrylamide, N,N-diethylaminoethylacrylamide, N,N-dimethylaminopropylacrylamide, N,N-diethylaminopropylacrylamide and corresponding methacrylamides. As a quaternary ammonium producing agent (or an agent for converting the tertiary amines into the quaternary ammonium salts), there can be used alkyl halides containing 1 to 4 carbon atoms or aralyl halides. It can be particularly preferable from the practical viewpoint to use a corresponding alkyl chloride or benzyl chloride.

In the process of the present invention, there is used, as a reaction medium, a mixture consisting of water and an aprotic organic solvent. In order to prevent not only the hydrolysis of the unsaturated quaternary amines but also the polymerization upon reaction for producing the quaternary salts, the ratio of charged materials is an important factor. Although the preferable ratio varies depending on the kinds of the unsaturated tertiary amines and the quaternary ammonium producing agent used, it can be preferable in general to use water and an aprotic organic solvent in a ratio of (120 to 5) : (10 to 60) [based on weight], per 100 parts by weight of the unsaturated tertiary amines. When water is charged in an amount exceeding 120 parts by weight, the hydrolysis of the tertiary amines tends to be accelerated, whereas when it is less than 5 parts by weight, the removal of heat from the reaction system and the stirring thereof becomes undesirably difficult since the unsaturated quaternary salts deposit with the progress of the reaction.

When an aprotic organic solvent is used in an amount less than 10 parts by weight, the polymerization during the reaction could be prevented only insufficiently, whereas when it is more than 60 parts by weight, enhanced effect could hardly be attained for the prevention of the polymerization and, rather, the load for removing the solvent after the reaction becomes excessively large.

In cases where the unsaturated tertiary amines represented by General Formula 1 are aminoesters or in cases where the quaternary ammonium salt producing agent is relatively liable to hydrolysis (e.g., in the case of benzyl chloride), it can be preferable to use water in a relatively small amount within the range described hereinabove and to add, after the completion of the reaction, additional water to the reaction product up to a desired concentration. In cases where the unsaturated tertiary amines are aminoamides or in cases where the quaternary salt producing agent is relatively resistant to hydrolysis (e.g., in the case of alkyl halides), it can be advantageous from the economic point of view to use water in a relatively large amount within the rang described hereinabove.

Examples of aprotic organic solvents applicable to the process of the invention include ketones, such as acetone and methyl ethyl ketone; halogenated solvents, such as trichloroethylene; aromatic compounds, such as benzene; fatty hydrocarbons, such as n-hexane; esters, such as ethyl acetate; and the like. In cases where, after the completion of the reaction, the product of the reaction is treated under reduced pressure to remove off the solvents used for the reaction and are utilized or marketed in the form of an aqueous solution, the use of acetone can be particularly preferable because of its low boiling point and high polarity.

It can be preferable to use an unsaturated tertiary amine, water and an aprotic organic solvent in the ratio as mentioned above. It is however possible to add, after the completion of the reaction, an additional water to the reaction product so as to adjust the concentration of the quaternary ammonium salts. Such an addition of water is by no means contrary to the gist of the present invention.

In the process of the invention, it is required to carry out the reaction under a condition that the concentration of dissolved oxygen is smaller than 1.8 ppm but not less than 0.3 ppm. If the concentration is not less than 1.8 ppm, polymerization inhibitors and gelation-causing substances are generated in large quantities and hence the object of the invention could not be achieved. When it is less than 0.3 ppm, it is not possible to prevent the polymerization of the tertiary amines and the produced quaternary ammonium salts even if the specific medium according to the invention is employed.

There is no particular limitation on the means for adjusting the concentration of oxygen dissolved in the reaction system to the above-described range. In general, it can be practical to replace the air in the reaction system with an inactive gas, such as nitrogen, helium, or the like.

The quaternary salt producing agent can be added to the reaction vessel prior to the start of the reaction. It is also possible to add the agent to the reaction vessel along with the progress of the reaction. The latter can be advantageous in order to prevent the reaction from proceeding beyond control. There is no particular limitation on the method how to add the agent to the reaction system. For example, it can be dropped at ordinary pressure or can be pressed into the reaction vessel.

There are no particular limitations on the other conditions for producing the quaternary ammonium salts, and the conditions can be selected within the known ranges. However, in the practice of the invention, the following conditions can be particularly effective, and it can be preferable to conduct the process in accordance with the following conditions. The temperature for producing the quaternary salts can be from 10° to 60° C., in particular, from 20° to 40° C. The quaternary salt producing agent is preferably used in an amount of from 1 to 1.2 mol, per mol of the tertiary amines. However, in cases where the agent could not be readily removed off after the reaction (for example, in the case where benzyl chloride is employed), it is possible to use the agent in an amount of from 0.95 t 1.0.

After the completion of the reaction, the reaction mixture may be allowed to separate into two layers (if necessary, water can be added thereto before or after the separation into two layers). The desired aqueous solution of the unsaturated quaternary ammonium salts can be obtained by treating the quaternary salt-containing layer under reduced pressure until the remaining organic solvent is removed off to a concentration where the polymerization of the ammonium salts would not be substantially inhibited by the solvent.

Additives, such as a polymerization inhibitor (for example, hydroquinone monomethyl ether, phenothiazine, and nitrobenzene), a chelating agent (for example, EDTA) and a pH regulator, can be added thereto before or after the reaction for producing the quaternary salts.

If desired, the thus obtained aqueous solution of the quaternary ammonium salts may be purified by using an ion exchange resin or activated carbon, or by means of solvent extraction.

BEST MODE FOR PRACTICING THE INVENTION

The present invention will further be illustrated by way of examples. It would however be understood that the invention is by no means limited thereto.

The measurement of the concentration of dissolved oxygen, the polymerization test and the measurement of solubility of the polymers were conducted as follows.

[1]Measurement of Concentration of Dissolved Oxygen

The concentration is measured by a diaphragm type galvanic cell dissolved oxygen meter.

[2]Polymerization Test Into a glass vessel equipped with a thermometer, a nitrogen gas introduction tube and a stirrer is charged a sample adjusted to a pH of 3.0 by the use of sulfuric acid, and the air in the reaction system is replaced with nitrogen gas. While being maintained at a temperature of 30° C., the sample is added with 50 ppm each (based on the weight of the pure sample) of ammonium persulfate, sodium bisulfite and 2,2-azobis(2-amidinopropane) dihydrochloride, and the polymerization behavior of the sample [polymerization induction time and the period of time required until the reaction mixture reaches to the maximum temperature (which is deemed to be the time required for the polymerization)]is determined.

[3]Measurement of Solubility of the Polymer

The polymerization product obtained in [2]is diluted with water up to a solid content of 0.2% by weight. Then, 1,000 g of the aqueous solution is filtered through a wire gauze of 150 mesh and the weight of gelated products is measured. The solubility of the polymer is determined as a weight of the wet gel (unit: g/g) per gram of said polymerized product (reduced to dry weight).

In the following examples, all the parts and percentages are based on weight unless otherwise specifically stated.

EXAMPLE 1

Into a 1 liter autoclave were charged 200 g (1.40 mol) of N,N-dimethylaminoethyl acrylate obtained by a conventional rectification under reduced pressure in an nitrogen atmosphere, 44.4 g of acetone and 0.4 g of hydroquinone monomethyl ether (polymerization inhibitor). After its internal temperature had been lowered to 20° C. or below, 22.2 g of distilled water was added thereto. The ratio of the charged materials was as follows: Dimethylaminoethyl acrylate : water : acetone =100 : 11.1 : 22.2. After adding water, the air in the reaction system was replaced with nitrogen gas until the concentration of dissolved oxygen had been lowered to 1.5 ppm, and then the reaction was allowed to start by introducing methyl chloride from a bomb at a pressure of 1.8 kg/cm$^2$. The reaction was allowed to proceed for 22 hours, during which the reaction temperature was so controlled that it would not exceed 40° C. After the reaction, the remaining pressure was released. The mixture contained 0.03% of free amines and 4 ppm of dissolved oxygen. After 45.4 g of water had been added thereto, the acetone contained in the resulting solution was removed off at reduced pressure at a temperature of 20° to 30° C. There was obtained 330 g of aqueous solution of unsaturated quaternary ammonium salt which contained 0.8 ppm of dissolved oxygen. The concentration of the quaternary ammonium salt contained in the product, the concentration of acrylic acid contained therein and its hue (APHA) (according to JIS-K-4104) were 81.8%, 0.07% and 10, respectively.

The polymerization induction time of the thus obtained quaternary ammonium salt was 11 minutes, and the time required for the polymerization was 46 minutes.

EXAMPLES 2-3, AND COMPARATIVE EXAMPLES 1-2

Aqueous solutions of unsaturated quaternary ammonium salts were obtained in the same manner as in Example 1, except that starting materials shown in Table 1 were used in quantities shown therein. The quality and the polymerization behavior of the products obtained are also shown in the table for the purpose of comparison. In Comparative Example 1 in which the concentration of dissolved oxygen exceeded the prescribed range according to the invention (from 0.3 to 1.8 ppm), impurities were generated in large quantities as indicated by the value of hue (APHA), which exceeded 200. As a result, the product obtained in the comparative example had a very poor polymerization characteristic. In Comparative Example 2 in which a non-aprotic organic solvent was used, the product started to polymerize during the reaction, and hence it was impossible to obtain any polymerized product usable in a practical use. It would therefore be apparent that the process of the invention is highly useful.

EXAMPLE 4

Into a 1 liter autoclave were charged 360 g (2.30 mol) of N,N-dimethylaminopropylacrylamide obtained by a conventional rectification under reduced pressure, 100 g of acetone and 1 g of hydroquinone monomethyl ether. After its internal temperature had been lowered to 20° C. or below, 119 g of water was added thereto. The ratio of the charged materials was as follows: Dimethylaminopropylacrylamide:water:acetone =100:33:28 (based on weight). After adding water, the air in the reaction system was replaced with nitrogen gas until the concentration of dissolved oxygen had been lowered to 0.4 ppm, and then the reaction was allowed to start by introducing methyl chloride from a bomb at a pressure of 1.4 to 1.5 kg/cm$^2$ The reaction was allowed to proceed for 20 hours at a reaction temperature not higher than 40° C. After the reaction, the remaining pressure was released, and the content of free amines was measured by means of sampling. The product contained 0.30% of free amines and the reaction rate was 99.65%. The reaction mixture was separated into two layers, and 32 g of acetone layer was removed off. The unsaturated quaternary ammonium salt-containing layer was treated under reduced pressure at a temperature of 20° to 30° C. to remove off the acetone contained therein. There was obtained 586 g of product.

The concentration of the unsaturated quaternary ammonium salt contained in the product and its hue (APHA) were 78.8% and 15, respectively. Divinyl compounds were not detected by gas chromatographic analysis.

The polymerization induction time of the thus obtained quaternary ammonium salt was 12 minutes, and the time required for its polymerization was 42 minutes. The polymerized product exhibited a good solubility to water, and no water insoluble gel was observed.

EXAMPLE 5

There was obtained 328 g of aqueous solution of unsaturated quaternary ammonium salt by repeating the procedure of Example 4 in the same manner, except that after the completion of the reaction, the reaction mixture was not separated into two layers to remove the acetone layer, and the reaction mixture was treated directly under reduced pressure under the same condition as in Example 4. The concentration of the unsaturated quaternary ammonium salt contained in the product and its hue (APHA) were 79.0% and 20, respectively. According to gas chromatography, the product contained 2.8 ppm of divinyl compounds.

The polymerization induction time of the thus obtained quaternary ammonium salt was 15 minutes, and the time required for the polymerization was 49 minutes. The polymerized product exhibited a good solubility to water, and no water insoluble gel was observed.

COMPARATIVE EXAMPLE 3

An aqueous solution of the same quaternary ammonium salt was prepared by repeating the procedure of Example 4 in the same manner, except that the reaction system was not replaced with nitrogen. During the reaction, the reaction system contained dissolved oxygen at a concentration of 8.9 ppm. The concentration of the quaternary ammonium salt contained in the thus obtained product and its hue (APHA) were 78.8% and 250, respectively.

According to gas chromatography, the product contained 38 ppm of divinyl compounds.

The polymerization induction time of the thus obtained quaternary ammonium salt was 47 minutes, and the time required for the polymerization was 210 minutes. The polymerization property of the product is therefore poor. The content of water insoluble gel was as much as 180 g/g. Accordingly, the solubility of the product is extremely poor.

COMPARATIVE EXAMPLE 4

The procedure of Example 4 was repeated, except that the air was reduced until the concentration of dissolved oxygen decreased to 0.1 ppm. However, polymerization started during the reaction of producing the quaternary salt and it became unable to conduct the subsequent procedure.

EXAMPLE 6 p Into a reaction vessel were charged 312 g of N,N-dimethylaminopropylacrylamide prepared by a conventional rectification under reduced pressure, 61 g of acetone and .4 g of phenothiazine. After its internal temperature had been lowered to 20° C. or below, 141.6 g of water was added thereto. After adding water, the air in the reaction system was replaced with nitrogen until the concentration of dissolved oxygen decreased to 1.2 ppm. The ratio of charged materials was as follows: N,N-dimethylaminopropylacryl-amide : water : acetone =100 : 45 : 20 (based on weight).

After its internal temperature had been lowered to 15° C., 253 g of benzyl chloride was dropped over a period of 1 hour, during which the reaction temperature was maintained at a temperature not exceeding 50° C.

After the completion of the dropping, the reaction was allowed to proceed for additional 1 hour at 40° C., and the concentration of free amines contained in the reaction mixture was measured by means of sampling. It contained 0.02% of free amines. The reaction mixture was treated under reduced pressure at 20° to 30° C. to remove the acetone. There was obtained 703 g of product. The concentration of quaternary ammonium salt contained in the product and its hue (APHA) were 79.9% and 40, respectively. No benzyl alcohol (which may be formed by the hydrolysis of benzyl chloride.) was detected by liquid chromatography. It contained 10 ppm of divinyl compounds.

COMPARATIVE EXAMPLE 5

The procedure of Example 6 was repeated, except that acetone was not charged at all. With the progress of the reaction, the viscosity of the reaction system increased markedly, and the stirring and the removal of heat became quite difficult. The required reaction time was three times as long as that in Example 6. After the completion of the reaction, the product contained 5.6% of free amines and had a hue (APHA) of 50. According to liquid chromatography, the concentration of benzyl alcohol (formed by the hydrolysis of benzyl chloride) was 1.92%, and the concentration of divinyl compounds was 25 ppm. The product is therefore of very poor quality in comparison with the product obtained in Example 6.

Availability in Industry

In cases where unsaturated quaternary ammonium salts represented by general formula II are produced by treating cationic monomers represented by General Formula I with an alkyl halide or an aralkyl halide in an aqueous medium according to the prior art, ammonium salts produced tend to polymerize when the concentration of dissolved oxygen is less than 1.8 ppm, whereas the production of by-products, such as gelation-causing substances (e.g., divinyl compounds) and trace amounts of polymerization inhibitors, could hardly be avoided when the concentration of the dissolved oxygen exceeds 1.8 ppm. However, when a mixture of water and an aprotic organic solvent is used as a reaction medium in accordance with the present invention, the reaction proceeds quite smoothly, without forming any deposition. The overheating of the reaction system, which is a cause for the polymerization and the side reactions, can be prevented effectively since the reaction system can be smoothly stirred and hence heat can be readily removed therefrom. In addition, the use of the organic solvent makes it possible to prevent the polymerization even with a low concentration of dissolved oxygen, and the generation of gelation-causing substance and the polymerization inhibitors can be suppressed. Accordingly, aqueous solutions of unsaturated quaternary ammonium salts that can be used as a raw material for producing cationic polymers of high molecular weight can be readily produced on a commercial scale in accordance with the process of the invention.

TABLE 1

| | Examples 2-3 and Comparative Examples 1-2 | | | | |
|---|---|---|---|---|---|
| | Items | Example 2 | Example 3 | Comparative Example 1 | Comparative Example 2 |
| Charging Conditions | Charged Amount of DMAEA* (g) | 200 | 200 | 200 | 200 |
| | Charged Amount of Water (g) | 22.2 | 22.2 | 22.2 | 67.6 |
| | Kind of Organic Solvent | Acetone | Ethyl Acetate | Acetone | None |
| | Organic Solvent Charged (g) | 88.8 | 44.4 | 44.4 | — |
| | Charged Ratio: | | | | |
| | DMAEA (Parts) | 100 | 100 | 100 | 100 |
| | Water (Parts) | 11.1 | 11.1 | 11.1 | 33.8 |
| | Acetone (Parts) | 44.4 | 22.2 | 22.2 | 0 |
| | Concentration of Dissolved Oxygen | 0.4 | 0.8 | 5.2 | 0.4 |
| Free Amines After Reaction (%) | | 0.04 | 0.08 | 0.04 | ** |
| Water Additionally added After Reaction (%) | | 45.4 | 45.4 | 45.4 | — |
| Quality of the Product | Concentration of Quaternary Ammonium Salt (%) | 81.4 | 81.3 | 81.4 | — |
| | Concentration of Acrylic Acid (%) | 0.05 | 0.07 | 0.07 | — |
| | Hue (APHA) | 10 | 15 | Above 200 | — |
| Polymerization Behavior | Polymerization Induction Time (Min.) | 10 | 14 | 48 | |
| | Time Required For Polymerization (Min.) | 45 | 49 | 220 | |

[Notes]
*N,N—dimethylaminoethyl acrylate
**Not Measurable because polymerization started during the reaction.

What is claimed is:

1. A process for producing unsaturated quaternary ammonium salts of very high quality represented by the following General Formula II:

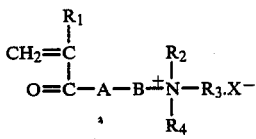

(in which $R_1$ represents a hydrogen atom or a methyl group; $R_2$ and $R_3$ each independently represents an alkyl group containing 1 to 4 carbon atoms; A represents an oxygen atom or an —NH—group; B represents an alkylene group containing 1 to 4 carbon atoms; $R_4$ represents an alkyl group containing 1 to 4 carbon atoms or a benzyl group; and $X^{31}$ represents a halogen atom) which comprises reacting a cationic vinyl monomer represented by the following General Formula I:

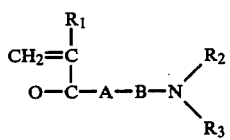

(in which $R_1$, $R_2$, $R_3$, A and B have the same meanings as defined above) with an alkyl halide or an aralkyl halide in a medium consisting of water and an aprotic organic solvent under a condition that the concentration of oxygen dissolved in the reaction system is lower than 1.8 ppm but not less than 0.3 ppm.

2. A process for producing unsaturated quaternary ammonium salts as defined in claim 1, wherein the ratio (by weight) of said cationic vinyl monomer, water and aprotic organic solvent charged is (100) : (5 to 120) : (10 to 60).

3. A process for producing unsaturated quaternary ammonium salts as defined in claim 1, wherein, after the completion of the reaction, said aprotic organic solvent used for the reaction is removed therefrom by, if desired after the reaction mixture was allowed to separate into two layers, treating the quaternary ammonium salt-containing layer under reduced pressure.

* * * * *